United States Patent
Roux et al.

[11] Patent Number: 6,103,259
[45] Date of Patent: Aug. 15, 2000

[54] PROCESS FOR THE PREPARATION OF LIPOSOMES WITHOUT THE USE OF AN ORGANIC SOLVENT

[75] Inventors: Didier Roux, Merignac; Corinne Degert, St. Medard en Jalles; René Laversanne, Pessac, all of France

[73] Assignee: Capsulis, Pessac, France

[21] Appl. No.: 09/069,844

[22] Filed: Apr. 30, 1998

Related U.S. Application Data

[63] Continuation of application No. 08/669,428, filed as application No. PCT/FR95/00012, Jan. 5, 1995, abandoned.

[30] Foreign Application Priority Data

Jan. 6, 1994 [FR] France .................................... 94 00090

[51] Int. Cl.⁷ .............................. A61K 9/127; A61K 7/00
[52] U.S. Cl. ...................... 424/450; 424/401; 428/402.2; 264/4.1; 264/4.3
[58] Field of Search ............................. 426/450; 264/4.1, 264/4.3; 424/401, 1.21, 9.321, 417, 94.3, 812; 428/402.2; 436/829; 935/54

[56] References Cited

U.S. PATENT DOCUMENTS 5,182,097  1/1993  Byron et al. .

FOREIGN PATENT DOCUMENTS

| 0 220 797 | 5/1987 | European Pat. Off. . |
| 0 299 937 | 1/1989 | European Pat. Off. . |
| 5-039484 | 2/1993 | Japan . |
| WO 88/06882 | 9/1988 | WIPO . |
| WO 90/00399 | 1/1990 | WIPO . |
| WO 91/04013 | 4/1991 | WIPO . |
| WO 93/19735 | 10/1993 | WIPO . |

OTHER PUBLICATIONS

D. Chapman, "Physicochemical Properties of Phospholipids and Lipid–Water Systems", Liposome Technology, vol. 1, pp. 1–19, 1984.

*Primary Examiner*—Gollamudi S. Kishore
*Attorney, Agent, or Firm*—Young & Thompson

[57] ABSTRACT

Multilamellar lipid vesicles are prepared by a two-step method. In the first step, a sterol is completely dissolved in a mixture comprising an aqueous solvent and a surfactant. In the second step, a lipid surfactant is added to a solution resulting from the first step, to prepare a homogeneous lamellar liquid crystal phase or a liquid crystal phase suspension in water. The liquid crystal phase or liquid crystal phase suspension can then be converted into multilamellar lipid vesicles.

19 Claims, No Drawings

PROCESS FOR THE PREPARATION OF LIPOSOMES WITHOUT THE USE OF AN ORGANIC SOLVENT

CROSS-REFERENCE TO RELATED APPLICATIONS

This application is a continuation of application Ser. No. 08/669,428, filed Jul. 31, 1996, now abandoned which was the 35 U.S.C. §371 national phase of International application PCT/FR95/00012 filed on Jan. 5, 1995, which designated the United States.

The present invention relates to a process for the preparation of liposomes without the use of an organic solvent.

Liposomes generally comprise a lipid surfactant as well as cholesterol and/or one/more encapsulated active product (s). The cholesterol (more generally a sterol) binds with the phospholipid to improve the elastic and impermeability properties of the lipid membrane. If the cholesterol or the active product to be encapsulated are mixed directly with the lipid and the aqueous solvent, the mixture remains non-homogeneous. For example, it can be observed that the cholesterol remains, after a number of days, in the form of small crystals which do not dissolve in the preparation, even with the addition of a large excess of water. In order to overcome this problem, a process known as "spraying" is used (see EP-A-87 993), which process comprises mixing the different constituents in an organic solvent (generally a chlorinated solvent, such as chloroform or dichloromethane; methanol is also used) before their use in an aqueous medium. Evaporation of this solvent produces a powder which is then used directly in the process for the preparation of liposomes (see, for example, EP-A-0 107 559). The disadvantage of this process is that passing through the spraying stage can leave traces (small but impossible to remove) of solvent in the final preparation. In view of the harmful effects of such traces on the health, it is essential to succeed in preparing liposomes without the use of an organic solvent.

Similar processes are used for incorporating membrane proteins in liposomes, that is to say proteins which are soluble in the membranes but which are difficult to dissolve in water.

The present invention is aimed at providing a process for the preparation of liposomes which makes it possible to avoid the spraying stage. The novelty of the process is based on the use of a well-chosen cosurfactant which makes it possible to dissolve the cholesterol or the active product to be encapsulated without the use of an organic solvent.

The subject of the present invention is therefore a process for the preparation of liposomes comprising:

1) the mixing of an aqueous solvent, of a surfactant comprising a hydrophilic head and a ($C_2$–$C_{16}$) hydrocarbon chain, of a sterol and/or a membrane protein and/or of a product to be encapsulated, so as to obtain dissolution of the sterol and/or of the product to be encapsulated;

2) the mixing of the composition thus obtained with a lipid surfactant, so as to form a homogeneous lamellar liquid crystal phase or a liquid crystal phase suspension in water, and 3) the conversion of the liquid crystal phase or of the liquid crystal phase suspension into liposomes.

It should be noted that, in certain cases, the conversion of the liquid crystal phase into liposomes takes place spontaneously.

The size of the spontaneous liposomes is typically from 100 to 500 nm, more generally from 50 to 5000 nm. The spontaneous liposomes obtained are multi-lamellar liposomes generally containing from 10 to 10,000 alternate layers of water and of surfactants (hydrophilic and lipophilic), including to the heart of the liposomes.

However, another subject of the invention is the liquid crystal phase or the liquid crystal phase suspension obtained in the second stage.

The present invention will now be described in more detail.

The surfactant used in the first stage comprises a branched or unbranched ($C_2$–$C_{16}$) carbon chain and preferably a ($C_6$–$C_{14}$) carbon chain.

The hydrophilic head is generally an alcohol or an ethoxylated alcohol but can also be a carboxylic acid or a salt of a fatty acid, a quaternary ammonium, a sulphonate or a sulphate or any other polar non-ionic or ionic group.

In the first stage, the aqueous solvent, the surfactant and the cholesterol and/or a membrane protein and/or the product to be encapsulated are mixed in suitable proportions. Generally, the surfactant is used in a proportion of 1 to 50% by weight, preferably of 5 to 25%, and the cholesterol in a proportion of 0% to 25% by weight. After stirring, the mixture is generally left standing for 1 to 2 hours. In certain cases, the cholesterol can be dissolved in this mixture with or without heating (40 to 100° Celsius) and stirring. This solubilization can last from a few hours to a few days. It is possible in certain cases also to dissolve first the cholesterol in the surfactant, when it is liquid (alcohol, ethoxylated alcohol, and the like), and then to add the aqueous solvent.

In the second stage, the lipid surfactant is added to the composition obtained in the first stage in the proportion necessary for the formation of a liquid crystal phase or of a liquid crystal phase suspension in water. Typically, from 1 to 50%, preferably from 5 to 25%, by weight of lipid surfactant is added. The lipid surfactant is preferably added in an amount greater than that of the surfactant used in the first stage. The lipid surfactant is selected from those conventionally used for the manufacture of liposomes and is generally a phospholipid. The mixture is generally stirred gently for 5 to 48 hours. If necessary, it can be maintained at a higher temperature, of about 60–80° Celsius, in order to accelerate the dissolving process. The mixture is then brought back to room temperature. In certain cases, the product to be encapsulated can be added at this point, just before adding the lipid surfactant.

A homogeneous lamellar liquid crystal phase or a liquid crystal phase suspension in an excess of water is thus obtained. The combined cholesterol and/or active product to be encapsulated have been dissolved. This paste may then be used to prepare liposomes according to a conventional method (ultrasound, extrusion) or by constant shearing, according to the process described in FR-A-2,689,418.

As indicated above, in certain cases spontaneous spherulites are formed without the need for additional steps. These spherulites can be easily characterized by phase contrast optical microscopy or ordinary optical microscopy when their size is sufficiently large and/or by cryofracture and electron microscopy. When the dosage results in the formation of spontaneous spherulites, the cream obtained after the second stage can be diluted directly in an aqueous solution and the liposomes, initially compactly piled up, separate and remain in dilute suspension. When an active product has been incorporated during the first stage, this product is found within the liposomes.

It should be noted, moreover, that the liposomes obtained can be dispersed in an oily phase. In this case, the dispersion is homogeneous after stirring for a few minutes. However, after a few hours, the liposomes end up settling out but can be resuspended by simple agitation. The oily phase which can be used can be, inter alia, a mineral oil or a vegetable oil.

The process according to the invention makes it possible to incorporate a substance which is active from the pharmaceutical or cosmetic viewpoint, which substance can be incorporated, depending on its nature, either in the aqueous parts or in the parts formed by the surfactants.

Mention may be made, as examples of active substances, of:

dihydroxyacetone (DHA), alpha-hydroxy acids (fruit acid) and more specifically glycolic, lactic, tartaric and salycilic acids, water-soluble and liposoluble sunscreening agents, essential oils, non-saponifiable compounds, sodium hyaluronate, micronized $TiO_2$, ceramides, caffeine, vitamins A, E and C.

The following examples illustrate the present invention.

EXAMPLE 1

1.5 g of pentaoxyethylene lauryl ether (C12E5) from the company Nikkol is dissolved in 7 g of water. 0.14 g of cholesterol (Merck) is added. Mixing is carried out and undissolved cholesterol crystals can clearly be seen with the eyes and under an optical microscope. The mixture is maintained at 80° for 12 hours in order to obtain complete dissolution of the cholesterol in the water/C12E5 mixture. The mixture can optionally be stirred occasionally or continuously, thus reducing the time for dissolving the cholesterol. The homogeneous mixture obtained is brought back to room temperature. 1.35 g of soya lecithin (Sigma) are then added, mixing is then carried out and, after waiting for 12 h, a homogeneous lamellar liquid crystal phase is obtained.

It can be confirmed, either by optical microscopy after diluting or by cryofracture and electron microscopy on the pure cream, that the mixture is composed of concentrated liposomes with a radius of approximately 200 to 500 nm. The mixture obtained may, in order to improve the size homogeneity, be treated directly (before diluting) according to the process described in FR-A-2 689 418.

EXAMPLE 2

The procedure is as in the preceding example, the same order being followed but with the following proportions:

2.5 g of C12E5

2.1 g of lecithin 0.4 g of cholesterol 5 g of water.

Liposomes are spontaneously obtained on completion of the second stage.

EXAMPLE 3

The procedure is as in Example 1 but with the following proportions:

0.5 g of C12E5

2.5 g of soya lecithin 0.25 g of cholesterol 6.75 g of water.

It is, however, necessary to wait at least 24 h at 60° in order to obtain a homogeneous mixture of water, C12E5 and cholesterol.

Liposomes are spontaneously obtained on completion of the second stage.

EXAMPLE 4

The procedure is as in Example 1 but the C12E5 from the company Nikkol is replaced by Lauropal from the company Witco (composed mainly of C12E5) and the following proportions are used:

1.1 g of Lauropal 0205

1.9 g of soya lecithin 0.2 g of cholesterol 6.8 g of water or 0.4 g of Lauropal 0205

2.6 g of soya lecithin 0.25 g of cholesterol 6.8 g of water.

EXAMPLE 5

The procedure is as in Example 1 but using another non-ionic surfactant: Lauropal 4 from the company Witco (composed mainly of C12E4) and the following proportions:

1.5 g of Lauropal 4

2.5 g of soya lecithin 0.25 g of cholesterol 6 g of water or 0.7 g of Lauropal 4

3.3 g of soya lecithin 0.33 g of cholesterol 6 g of water

EXAMPLE 6

The procedure is as in Example 1, using another non-ionic surfactant: Remcopal 121 from the company CECA (composed mainly of C12E3) and the following proportions:

0.7 g of Remcopal 121

3 g of soya lecithin 0.33 g of cholesterol 6 g of water or 0.5 g of Remcopal 121

3 g of soya lecithin 0.35 g of cholesterol 6 g of water.

EXAMPLE 7

The procedure is as in Example 1, using:

1 g of potassium oleate (Aldrich)

3 g of soya lecithin 0.3 g of cholesterol 6 g of water or 0.5 g of potassium oleate 3.5 g of soya lecithin 0.35 g of cholesterol 6 g of water.

EXAMPLE 8

A $10^{-3}$ molar concentration of calcein is incorporated in the water of preparation of Example 4 (second composition).

It is possible, after preparation, to confirm that the fluorescent probe (calcein) has indeed been incorporated by measuring the kinetics of decline of fluorescence by extinction with cobalt.

EXAMPLE 9

2.5 g of Remcopal 121 (CECA) and 0.8 g of cholesterol (Aldrich) are placed in an erlenmeyer flask. 4 g of water are added, mixing is carried out, the mixture is then left standing for 2 to 3 hours at 65° C. until the cholesterol has completely dissolved and the mixture is allowed to cool to room temperature. 10 g of Phospholipon 90P lecithin (Nattermann) are added, mixing is carried out for a few minutes, 8.5 g of an aqueous solution containing 40% by weight of DHA (Merck) are added dropwise and the pH is adjusted to 3 with hydrochloric acid. Intimate mixing is carried out, in order to obtain a homogeneous paste, which is left standing for 24 h at room temperature.

This paste can then be diluted in water in order to obtain a homogeneous suspension of capsules containing DHA. The pH is then adjusted to pH=5, which makes it possible to have an external formulation of the capsules at this pH while retaining the DHA in the capsules at a more acidic pH. pH measurements and quantitative determinations as a function of time make it possible to confirm that the degradation of the DHA is slowed down when the latter is microencapsulated, with respect to a simple aqueous solution.

EXAMPLE 10

2.5 g of Remcopal 121 and 0.8 g of cholesterol are placed in an erlenmeyer flask. 4 g of water are added, mixing is carried out and the mixture is then left standing for 2 to 3 hours at 65° C. until the cholesterol has completely dissolved. The mixture is allowed to cool to room temperature. 10 g of Phospholipon 90P lecithin and 1 g of salicylic acid (Aldrich) are added. Mixing is carried out for a few minutes and 7 g of an aqueous solution containing 42 mg of a sodium salt of methyl para-hydroxybenzoate, 89 mg of a sodium salt of propyl para-phydroxybenzoate and 127 mg of 2-phenoxyethanol (Aldrich) are added dropwise. Mixing is carried out for a few minutes and the mixture is left standing for 24 h at 37° C. This homogeneous paste can then be dispersed in water to form multilamellar liposomes containing salicylic acid. Separation by centrifuging and then quantitative determination makes it possible to show that more than 70% of the acid is contained in the capsules. The addition of a coloured indicator to the preparation makes it possible to show, on carrying out an acid/base titration, that the interior of the capsules is at a pH approximately 2 pH units lower than the outside.

EXAMPLE 11

2.5 g of Remcopal 121 and 0.8 g of cholesterol are placed in an erlenmeyer flask. 4 g of water are added, mixing is carried out, the mixture is then left standing for 2 to 3 hours at 65° C. until the cholesterol has completely dissolved and the mixture is allowed to cool to room temperature. 10 g of Phospholipon 90P lecithin are added. Mixing is carried out for a few minutes and 8.5 g of an aqueous solution containing 1% of sodium hyaluronate (Laboratoire Bomann) are added drop-wise. The mixture is left standing for 24 h. This mixture can be dispersed in water in order to obtain an aqueous suspension of capsules containing sodium hyaluronate.

The mixture can also be dispersed in castor oil and a homogeneous suspension of capsules can be obtained, which suspension can be used in future preparations. However, after a few hours, the capsules settle out but can be resuspended by simple agitation.

EXAMPLE 12 (water-soluble sunscreening agent)

An aqueous phase containing 10% of Eusolex 232 (Merck) is prepared: phase A.

2.3 g of Remcopal 121 and 0.8 g of cholesterol are placed in an erlenmeyer flask, 4 g of water are added, mixing is carried out, the mixture is then left standing for 2 to 3 hours at 65° C. until the cholesterol has completely dissolved and the mixture is allowed to cool to room temperature. 11.3 g of Phospholipon 25P lecithin (Nattermann) are added. Mixing is carried out for a few minutes and 7 g of phase A are added dropwise. The mixture is allowed to stand for 24 h. The preparation can be dispersed in water or oil in order to obtain a suspension of capsules containing the sunscreening agent.

EXAMPLE 13 (oil-soluble sunscreening agent).

6 g of Remcopal 121 and 1.5 g of cholesterol are placed in an erlenmeyer flask, 8 g of water are added, mixing is carried out and the mixture is then left to stand for 2 to 3 hours at 65° C. until the cholesterol has completely dissolved. The mixture is allowed to cool to room temperature. 18 g of Phospholipon 25P lecithin are added. 6 g of methoxycinnamate are added, mixing is carried out for a few minutes and 16 g of water are added dropwise. The preparation is left standing for 24 h and can be dispersed in water in order to obtain a suspension of capsules containing the sunscreening agent.

What is claimed is:

1. A method for preparing multilamellar lipid vesicles incorporating a sterol comprising the steps of:
    a) dissolving, in a first step, said sterol in a mixture comprising an aqueous solvent and a surfactant comprising a hydrophilic head and a $(C_2-C_{16})$ hydrocarbon chain, wherein said sterol is completely dissolved in said mixture as a first solution,
    b) adding a lipid surfactant to said first solution to prepare, in a second step, a homogeneous lamellar liquid-crystal phase or a liquid crystal-phase suspension in water, comprising said first solution and the lipid surfactant, and
    c) converting said liquid-crystal phase or said liquid-crystal phase suspension into multilamellar lipid vesicles.

2. The method according to claim 1, in which the surfactant used in the first step has a $(C_6-C_{14})$ hydrocarbon chain.

3. The method according to claim 1, wherein said sterol is cholesterol.

4. The method according to claim 3, in which, in the first step, a mixture comprising 1 to 50% by weight of surfactant and 25% by weight or less of cholesterol is used.

5. The method according to claim 1, wherein the lipid surfactant is a phospholipid surfactant.

6. The method according to claim 2, in which, in the first step, a mixture comprising 5 to 20% by weight of surfactant is used.

7. The method according to claim 1, in which, in the second step, 1 to 50% of lipid surfactant is added.

8. The method according to claim 7, in which, in the second step, 5 to 50% by weight of lipid surfactant is added.

9. The method according to claim 1, in which the lipid surfactant is added in an amount greater than that of the surfactant used in the first step.

10. The method according to claim 1, further comprising a step of dispersion of the multilamellar vesicles.

11. The method according to claim 1, wherein said multilamellar vesicles are dispersed in water.

12. The method according to claim 1, wherein said multilamellar vesicles are dispersed in an oily phase.

13. A multilamellar lipid vesicle prepared by the method of claim 1, incorporating a sterol and comprising, as essential surfactive components, a first surfactant comprising a hydrophilic head and a ($C_2$–$C_{16}$) hydrocarbon chain and a second surfactant which is a lipid surfactant.

14. The multilamellar lipid vesicle according to claim 13, wherein said first surfactant has a ($C_6$–$C_{14}$) hydrocarbon chain.

15. The multilamellar lipid vesicle according to claim 13, wherein said sterol is cholesterol.

16. The multilamellar lipid vesicle according to claim 13, wherein the lipid surfactant is a phospholipid surfactant.

17. The multilamellar lipid vesicle according to claim 13, in which the lipid surfactant is present in an amount greater than that of the first surfactant.

18. A composition comprising a dispersion of multilamellar vesicles according to claim 13.

19. A method for preparing a lipid crystal phase or a lipid crystal phase suspension comprising a sterol which comprises the steps of:

a) dissolving, in a first step, said sterol in a mixture comprising an aqueous solvent and a surfactant comprising a hydrophilic head and a ($C_2$–$C_{16}$) hydrocarbon chain, wherein said sterol is completely dissolved in said mixture as a first solution, and b) adding a lipid surfactant to said first solution to prepare, in a second step, a homogeneous lamellar liquid-crystal phase or a liquid-crystal phase suspension in water comprising said first solution and the lipid surfactant.

* * * * *